United States Patent
Patel

Patent Number: 5,319,109
Date of Patent: Jun. 7, 1994

[54] POLYCYCLIC DYES

[75] Inventor: Prakash Patel, Edgerton, England

[73] Assignee: Zeneca Limited, London, England

[21] Appl. No.: 25,654

[22] Filed: Mar. 3, 1993

[30] Foreign Application Priority Data

Jun. 3, 1992 [GB] United Kingdom ............ 9204904

[51] Int. Cl.$^5$ ............................................ C07D 493/04
[52] U.S. Cl. .................................................. 549/299
[58] Field of Search ........................................ 549/299

[56] References Cited

FOREIGN PATENT DOCUMENTS 0146269 6/1985 European Pat. Off. .
0363034 4/1990 European Pat. Off. .
0397170 11/1990 European Pat. Off. .

Primary Examiner—C. Warren Ivy
Assistant Examiner—A. A. Owens
Attorney, Agent, or Firm—Cushman, Darby & Cushman

[57] ABSTRACT

A polycyclic dye of the Formula (1):

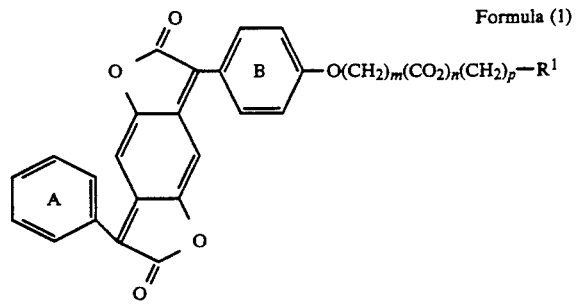

Formula (1)

wherein:
Ring A is unsubstituted or is substituted by from 1 to 3 groups;
$R^1$ is cycloalkyl;
m is 0, 1, 2 or 3;
n is 0 or 1;
p is 0, 1, 2 or 3; and
Ring B is unsubstituted apart from the $-O(CH_2)_m(CO_2)_n(CH_2)_p-R^1$ or is substituted by from 1 to 4 further groups.

The dyes are useful for the coloration of textile materials particularly synthetic textiles such as polyester.

5 Claims, No Drawings

POLYCYCLIC DYES

This specification describes an invention which relates to polycyclic dyes.

According to the present invention there is provided a polycyclic dye of the Formula (1):

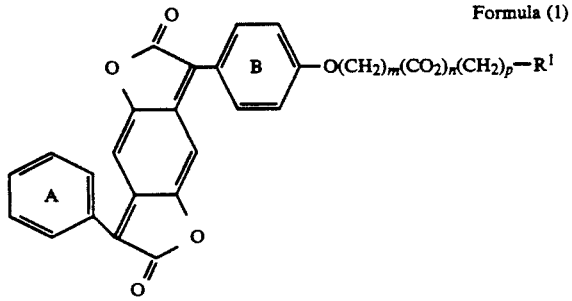

Formula (1)

wherein:
Ring A is unsubstituted or is substituted by from 1 to 3 groups;
$R^1$ is cycloalkyl;
m is 0, 1, 2 or 3;
n is 0 or 1;
p is 0, 1, 2 or 3; and
Ring B is unsubstituted apart from the $-O(CH_2)_m(CO_2)_n(CH_2)_p-R^1$ or is substituted by from 1 to 4 further groups.

Suitable further substituents for Ring B are preferably selected from —OH, halogen, nitro, alkyl, alkoxy, alkenyl, aryl, alkoxyalkyl, alkoxyalkoxy, alkoxycarbonylalkoxy, alkoxyalkoxycarbonylalkoxy, alkylcarbonyloxyalkoxy, aryloxy, alkylcarbonyl, alkylsulphonyl, CN-alkoxy, HO-alkoxy, $HO_2C$-alkoxy, alkylthio, arylthio and $-NR^2R^3$ in which $R^2$ and $R^3$ are each independently —H, alkyl or alkenyl.

Suitable substituents for Ring A are those listed for Ring B above and $-O(CH_2)_m(CO_2)_n(CH_2)_p-R^1$ in which m, n, p and $R^1$ are as hereinbefore defined.

In the substituents for Ring A and Ring B it is preferred that the alkyl or alkoxy parts of the substituents are $C_{1-4}$-alkyl or $C_{1-4}$-alkoxy respectively, the alkenyl is $C_{3-4}$-alkenyl, the aryl is phenyl or naphthyl, and the halogen is —F, —Cl or —Br. Preferred substituents for Ring A are $C_{1-4}$-alkyl, $C_{1-4}$-alkoxy, $-NH_2$ or $-NHC_{1-4}$-alkyl. Especially preferred substituents for Ring A are $C_{1-4}$-alkyl, $C_{1-4}$-alkoxy, $-NH_2$ and $-NHC_{1-4}$-alkyl in the 4-position and —H or $C_{1-4}$-alkyl in the 3-position. Where Ring A is substituted by one further substituent it is preferred that this is in the 3-, 4- or 5-position, more preferably in the 4-position. Where Ring A is substituted by two further substituents it is preferred that these are in the 3- and 4-positions, and where there are three further substituents it is preferred that these are in the 3-, 4- and 5-positions. Ring B is preferably unsubstituted, apart from the $-O(CH_2)_m(CO_2)_n(CH_2)_p-R^1$ group, or is substituted by one or two further substituents and these substituents are preferably in the 3- or in the 3- and 5-positions.

The alkyl or alkoxy substituents suitable for Ring A and Ring B may be straight or branched chain.

The cycloalkyl group represented by $R^1$ is preferably a $C_{3-8}$-cycloalkyl group, more preferably $C_{5-7}$-cycloalkyl and especially cyclohexyl. The cycloalkyl group represented by $R^1$ may be substituted by at least one group selected from $C_{1-6}$-alkyl, $C_{1-6}$-alkoxy, hydroxy, cyano, halogen, such as —Cl and —F, nitro, $C_{1-4}$-alkoxy-$C_{1-4}$-alkoxy, $C_{1-4}$-alkylcarbonyl, $C_{1-4}$-alkoxycarbonyl, $C_{1-4}$-alkoxy-$C_{1-4}$-alkoxycarbonyl, $C_{1-4}$-alkylcarbonyloxy, $C_{1-4}$-alkoxycarbonyloxy, $C_{1-4}$-alkoxy-$C_{1-4}$-alkoxycarbonyloxy, phenyl, amino, $C_{1-4}$-alkylamino and di($C_{1-4}$-alkyl)amino.

A preferred sub-group of compounds of Formula (1) are those in which m is from 1 to 3, n is 1, p is from 1 to 3, and $R^1$, Ring A and Ring B are as hereinbefore defined. A further preferred sub-group of compounds of Formula (1) are those in which m is from 1 to 3, n is 0, p is from 1 to 3, and $R^1$, Ring A and Ring B are as hereinbefore defined.

Especially preferred compounds of Formula (1) are those in which $R^1$ is cyclohexyl, Ring A is unsubstituted or is substituted by $C_{1-4}$-alkoxy, m is 1 or 2, n is 1 and p is from 1 to 3 and those in which $R^1$ is cyclohexyl, Ring A is unsubstituted or is substituted by $C_{1-4}$-alkoxy, m is from 1 to 3, n is 0 and p is 0.

The compounds of Formula (1) in which n is 1 may be prepared by esterification of the corresponding carboxylic acid to that of Formula I in which $-(CH_2)_p-R^1$ is replaced by H with for example an alcohol of formula $HO(CH_2)_p-R^1$ in which p and $R^1$ are as hereinbefore defined. The compounds of Formula (1) in which n is 0 may be prepared by alkylation of the corresponding hydroxy compound to that of Formula I in which $-(CH_2)_m(CO_2)_n(CH_2)_p-R^1$ is replaced by H in an aprotic solvent such as dimethylformamide or sulpholane with an alkylating agent such as a mesylate of formula $MeSO_2O(CH_2)_m(CH_2)_p-R^1$, in which Me is methyl and m, p and $R^1$ are as hereinbefore defined.

The carboxylic acid and hydroxy compounds referred to above may be prepared by methods described in EP 0033583B and 0146269B and in EP 0363034A.

Compounds of Formula (1) give yellowish-red to bluish-red shades when applied to synthetic fibers or mixtures thereof, especially polyesters by disperse dyeing processes. The compounds of Formula (1) exhibit excellent fastness properties.

The invention is further illustrated by the following examples:

EXAMPLE 1

(i) A mixture of hydroquinone (15 g), mandelic acid (15 g), acetic acid (95 cm³) and sulphuric acid (5 cm³) was stirred at ambient temperature before filtering off solid material. The solid was washed with water and dried to give 5-hydroxy-2-oxo-3-phenyl-2,3-dihydrobenzofuran (14 g, 65%).

(ii) A mixture of 5-hydroxy-2-oxo-3-phenyl-2,3-dihydrobenzofuran (14 g), 4-carboxymethoxymandelic acid (18 g), acetic acid (100 cm³) and sulphuric acid (100 cm³) was heated at 110° C. for 18 hours before cooling. Ammonium persulphate (13.5 g) was added and the mixture heated at 110° C. for 1 hour. The reaction mixture was cooled and poured into a mixture of ice and water, the precipitated solid was filtered off, washed with water and methanol and dried to give 3-phenyl-7-(4-(carboxymethoxy)phenyl)-2,6-dioxo-2,6-dihydrobenzo-[1:2-b, 4:5-b']difuran (10.5 g, 45%).

(iii) A mixture of 3-phenyl-7-(4-(carboxymethoxy)-phenyl)-2,6-dioxo-2,6-dihydrobenzo-[1:2-b, 4:5-b']difuran (2 g), cyclohexylmethanol (20 cm³) and sulphuric acid (98%, 0.25 cm³) was heated at 180° C. for 1½ hours. The reaction mixture was cooled, the precipitated solid was filtered off, washed with methanol and dried. The dried solid was recrystallised from toluene to give 3-phenyl-7-(4-(cyclohexylmethoxycarbonylmethoxy) phenyl)-2,6-dioxo-2,6-dihydrobenzo-[1:2-b, 4:5-b']difuran (1.6 g, 65%). $\lambda_{max}$ in dichloromethane=488 nm.

EXAMPLE 2

The procedure of Example 1(iii) was followed except that 2-(cyclohexyl)ethanol was used in place of the cyclohexylmethanol. 3-Phenyl-7-(4-(2-cyclohexylethoxycarbonylmethoxy)phenyl)-2,6-dioxo-2,6-dihydrobenzo-[1:2-b, 4:5-b']difuran (2 g, 79%) was obtained. $\lambda_{max}$ in dichloromethane=484 nm.

EXAMPLE 3

The procedure of Example 1(iii) was followed except that 3-(cyclohexyl)propanol was used in place of the cyclohexylmethanol. 3-Phenyl-7-(4-(3-cyclohexylpropoxycarbonylmethoxy)phenyl)-2,6-dioxo-2,6-dihydrobenzo-[1:2-b, 4:5-b']difuran (1.8 g, 69%) was obtained. A $\lambda_{max}$ in dichloromethane=484 nm.

EXAMPLE 4

(i) The procedure of Example 1(i) was followed except that 4-(n-propoxy)mandelic acid was used in place of mandelic acid. 5-Hydroxy-2-oxo-3-(4-n-propoxyphenyl)-2,3-dihydrobenzofuran was obtained.

(ii) The procedure of Example 1(ii) was followed except that 4-(n-propoxy)mandelic acid was used in place of mandelic acid. 5-hydroxy-2-oxo-3-(4-(n-propoxy)-phenyl)-2,4-dihydrobenzofuran was used obtained.

(ii) The procedure of Example 1(ii) was followed except that 5-hydroxy-2-oxo-3-(4-(n-propoxy)phenyl)-2,4-dihydrobenzofuran was used in place of 5-hydroxy-2-oxo-3-phenyl-2,3-dihydrobenzofuran. 3-(4-(n-Propoxy)phenyl)-7-(4-(carboxymethoxy)phenyl)-2,6-dioxo-2,6-dihydrobenzo-[1:2-b, 4:5-b']difuran was obtained.

(iii) The procedure of Example 1(iii) was followed except that 3-(4-(n-propoxy)phenyl)-7-(4-(carboxymethoxy)phenyl)-2,6-dioxo-2,6-dihydrobenzo-[1:2-b, 4:5-b']difuran (3 g) was used in place of the 3-phenyl-7-(4-(carboxymethoxy)phenyl)-2,6-dioxo-2,6-dihydrobenzo-[1:2-b, 4:5-b']difuran. 3-(4-(n-Propoxy)-phenyl)-7-(4-(cyclohexylmethoxycarbonylmethoxy)-phenyl)-2,6-dioxo-2,6-dihydrobenzo-[1:2-b, 4:5-b']difuran (2 g, 56%) was obtained $\lambda_{max}$ in dichloromethane=518 nm.

EXAMPLE 5

The procedure of Example 4 was followed except that 2-(cyclohexyl)ethanol was used in place of the cyclohexylmethanol. 3-(4-(n-Propoxy)phenyl)-7-(4-(2-cyclohexylethoxycarbonylmethoxy)phenyl)-2,6-dioxo-2,6-dihydrobenzo-[1:2-b, 4:5-b']difuran (2.1 g, 57%) was obtained. $\lambda_{max}$ in dichloromethane=519 nm.

EXAMPLE 6

The procedure of Example 4 was followed except that 3-(cyclohexyl)propanol was used in place of the cyclohexylmethanol. 3-(4-(n-Propoxy)phenyl)-7-(4-(3-cyclohexylpropoxycarbonylmethoxy) phenyl)-2,6-dioxo-2,6-dihydrobenzo-[1:2-b, 4:5-b']difuran (2.2 g, 58%) was obtained. $\lambda_{max}$ in dichloromethane=518 nm.

EXAMPLE 7

A mixture of 3-phenyl-7-(4-hydroxyphenyl)-2,6-dioxo-2,6-dihydrobenzo-[1:2-b, 4:5-b']difuran (5 g), potassium carbonate (1.9 g), cyclohexylpropylmesylate (3 g) and sulpholane (100 cm$^3$) were stirred at ambient temperature before heating at 160° C. for ½ hour. The reaction mixture was cooled, water was added and the precipitated solid filtered off, washed with water and dried. The dry solid was dissolved in dichloromethane and the resultant solution was filtered to remove insoluble matter before purification by elution from silica and recrystallising from toluene. 3-Phenyl-7-(4-(3-cyclohexylpropoxy) phenyl)-2,6-dioxo-2,6-dihydrobenzo[1:2-b, 4:5-b']difuran (1.5 g, 22%) was obtained. A $\lambda_{max}$ in dichloromethane=500 nm.

EXAMPLES 8–25

The procedure of Example 1 was used to prepare the following dyes of Formula (2):

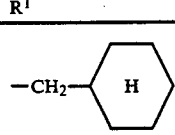

Formula (2)

| EXAMPLE | R$^1$ | R$^5$ | R$^6$ | $\lambda_{max}$ nm |
|---|---|---|---|---|
| 8 | —CH$_2$—H | —OC$_2$H$_5$ | —H | 516 |
| 9 | —CH$_2$—H | —CH$_3$ | —H | 500 |
| 10 | —CH$_2$—H | —NH$_2$ | —H | 572 |
| 11 | —CH$_2$—H | —NH$_2$ | —CH$_3$ | 570 |
| 12 | —CH$_2$—H | —NHC$_2$H$_5$ | —CH$_3$ | 621 |
| 13 | —CH$_2$—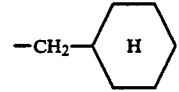H | —OC$_2$H$_5$ | —CH$_3$ | 520 |
| 14 | —C$_2$H$_4$—H | —OC$_2$H$_5$ | —H | 513 |

-continued

Formula (2)

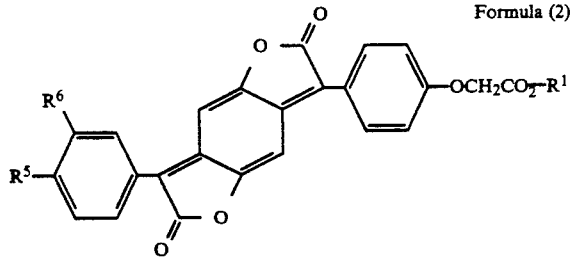

| EXAMPLE | R¹ | R⁵ | R⁶ | λmax nm |
|---|---|---|---|---|
| 15 | $-C_2H_4-$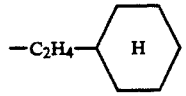 | $-CH_3$ | $-H$ | 498 |
| 16 | $-C_2H_4-$ cyclohexyl | $-NH_2$ | $-H$ | 571 |
| 17 | $-C_2H_4-$ cyclohexyl | $-NHC_2H_5$ | $-CH_3$ | 618 |
| 18 | $-C_2H_4-$ cyclohexyl | $-OC_2H_5$ | $-CH_3$ | 519 |
| 19 | $-C_2H_4-$ cyclohexyl | $-NH_2$ | $-CH_3$ | 567 |
| 20 | $-C_3H_6-$ cyclohexyl | $-OC_2H_5$ | $-H$ | 517 |
| 21 | $-C_3H_6-$ cyclohexyl | $-CH_3$ | $-H$ | 501 |
| 22 | $-C_3H_6-$ cyclohexyl | $-NH_2$ | $-H$ | 569 |
| 23 | $-C_3H_6-$ cyclohexyl | $-NH_2$ | $-CH_3$ | 570 |
| 24 | $-C_3H_6-$ cyclohexyl | $-NHC_2H_5$ | $-CH_3$ | 619 |

-continued

Formula (2)

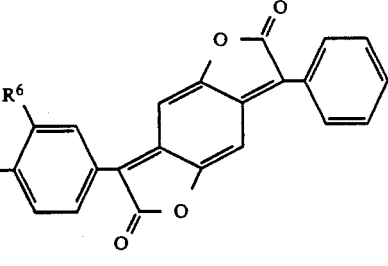

| EXAMPLE | R¹ | R⁵ | R⁶ | λmax nm |
|---|---|---|---|---|
| 25 | $-C_3H_6-$ cyclohexyl | $-OC_2H_5$ | $-CH_3$ | 518 |

—cyclohexyl = cyclohexyl.

EXAMPLES 26–40

The procedure of Example 7 was used to prepare the following dyes of Formula (3):

Formula (3)

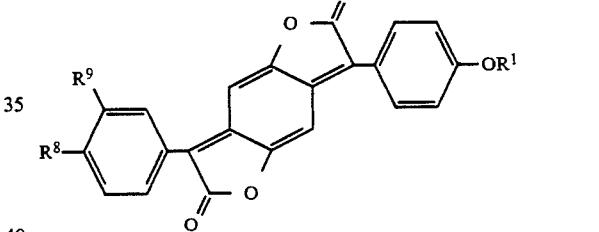

| EXAMPLE | R¹ | R⁸ | R⁹ | λmax nm |
|---|---|---|---|---|
| 26 | $-CH_2-$ cyclohexyl | $-OC_3H_7$ | $-H$ | 533 |
| 27 | $-CH_2-$ cyclohexyl | $-H$ | $-H$ | 499 |
| 28 | $-CH_2-$ cyclohexyl | $-CH_3$ | $-H$ | 510 |
| 29 | $-CH_2-$ cyclohexyl | $-NH_2$ | $-H$ | 578 |
| 30 | $-CH_2-$ cyclohexyl | $-NH_2$ | $-CH_3$ | 580 |

-continued

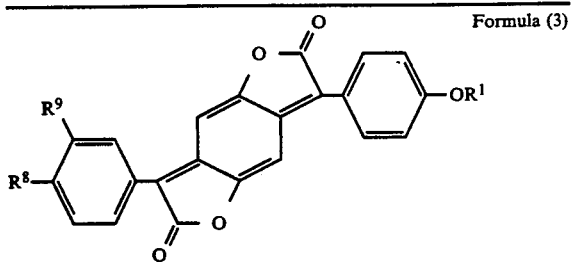

Formula (3)

| EXAMPLE | R¹ | R⁸ | R⁹ | λmax nm |
|---|---|---|---|---|
| 31 | —C₂H₄—H(cyclohexyl) | —H | —H | 499 |
| 32 | —C₂H₄—H(cyclohexyl) | —OC₃H₇ | —H | 537 |
| 33 | —C₂H₄—H(cyclohexyl) | —CH₃ | —H | 512 |
| 34 | —C₂H₄—H(cyclohexyl) | —NH₂ | —H | 579 |
| 35 | —C₂H₄—H(cyclohexyl) | —NH₂ | —CH₃ | 582 |
| 36 | —C₃H₆—H(cyclohexyl) | —OC₃H₇ | —H | 539 |
| 37 | —C₃H₆—H(cyclohexyl) | —CH₃ | —H | 512 |
| 38 | —C₃H₆—H(cyclohexyl) | —NH₂ | —H | 580 |
| 39 | —C₃H₆—H(cyclohexyl) | —NH₂ | —CH₃ | 581 |
| 40 | —C₃H₆—H(cyclohexyl) | —NHC₂H₅ | —CH₃ | 616 |

—H(cyclohexyl symbol) = cyclohexyl.

I claim:

1. A polycyclic dye of the Formula (1):

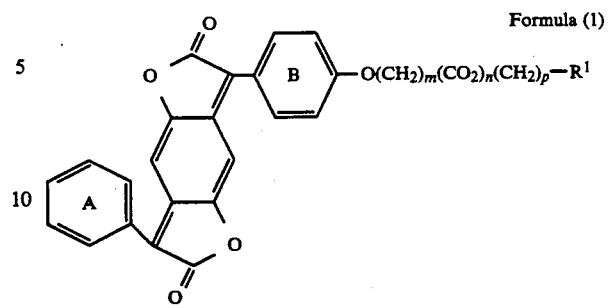

Formula (1)

wherein:
Ring B is unsubstituted apart from the —O(CH$_2$)$_m$-(CO$_2$)$_n$(CH$_2$)$_p$—R$^1$ or is substituted by from 1 to 4 further groups selected from the group consisting of —OH, —F, —Cl, —Br, nitro, C$_{1-4}$-aklyl, C$_{1-4}$-alkoxy, C$_{3-4}$-alkenyl, phenyl, naphthyl, C$_{1-4}$-alkoxyC$_{1-4}$-alkyl, C$_{1-4}$-alkoxyC$_{1-4}$-alkoxy, C$_{1-4}$-alkoxycarbonylC$_{1-4}$-alkoxy, C$_{1-4}$-alkoxyC$_{1-4}$-alkoxy carbonylC$_{1-4}$-alkoxy, C$_{1-4}$-alkylcarbonyloxyC$_{1-4}$-alkoxy, phenoxy, naphthoxy, C$_{1-4}$-alkylcarbonyl, C$_{1-4}$-alkylsulphonyl, CN—C$_{1-4}$-alkoxy, HO—C$_{1-4}$-alkoxy, HO$_2$C—C$_{1-4}$-alkoxy, C$_{1-4}$-alkylthio, phenylthio, naphthylthio and —NR$^2$R$^3$ in which R$^2$ and R$^3$ are each independently —H, C$_{1-4}$-alkyl or C$_{3-4}$alkenyl,
R$^1$ is C$_{3-8}$-cycloakyl;
m is from 1 to 3;
n is 1;
p is from 1 to 3; and
Ring A is unsubstituted or is substituted by from 1 to 3 groups selected from any of the substituents defined for Ring B above and the group —O(CH$_2$)$_{m'}$-(CO$_2$)$_{n'}$(CH$_2$)$_{p'}$—R$^1$ in which m' is 0, 1, 2 or 3, n' is 0 or 1, p' is 0, 1, 2 or 3.

2. A polycyclic dye of the Formula (1):

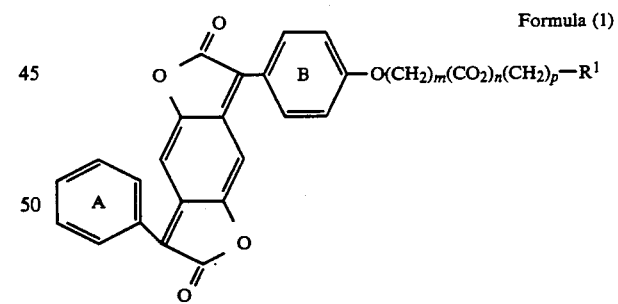

Formula (1)

wherein:
Ring B is unsubstituted apart from the —O(CH$_2$)$_m$-(CO$_2$)$_n$(CH$_2$)$_p$—R$^1$ or is substituted by from 1 to 4 further groups selected from the group consisting of —OH, —F, —Cl, —Br, nitro, C$_{1-4}$-aklyl, C$_{1-4}$-alkoxy, C$_{3-4}$-alkenyl, phenyl, naphthyl, C$_{1-4}$-alkoxyC$_{1-4}$-alkyl, C$_{1-4}$-alkoxyaC$_{1-4}$-alkoxy, C$_{1-4}$-alkoxycarbonylC$_{1-4}$-alkoxy, C$_{1-4}$-alkoxyC$_{1-4}$-alkoxy carbonylC$_{1-4}$-alkoxy, C$_{1-4}$-alkylcarbonyloxyC$_{1-4}$-alkoxy, phenoxy, naphthoxy, C$_{1-4}$-alkylcarbonyl, C$_{1-4}$-alkylsulphonyl, CN—C$_{1-4}$-alkoxy, HO—C$_{1-4}$-alkoxy, HO$_2$C—C$_{1-4}$-alkoxy, C$_{1-4}$-alkylthio, phenylthio, naphthylthio and —NR$^2$R$^3$ in which R$^2$ and $R^3$ are each independently —H, $C_{1-4}$-alkyl or $C_{3-4}$alkenyl, $R^1$ is $C_{3-8}$-cycloakyl;

m is from 1 to 3;

n is 0;

p is from 1 to 3; and

Ring A is unsubstituted or is substituted by from 1 to 3 groups selected from any of the substituents defined for Ring B above and the group —O(CH$_2$)$_{m'}$-(CO$_2$)$_{n'}$(CH$_2$)$_{p'}$—$R^1$ in which m' is 0, 1, 2 or 3, n' is 0 or 1, p' is 0, 1, 2 or 3.

3. A polycyclic dye according to claim 1 wherein $R^1$ is cyclohexyl, Ring A is unsubstituted or is substituted by $C_{1-4}$-alkoxy, m is 1 or 2, n is 1 and p is from 1 to 3.

4. A polycyclic dye of the Formula (1):

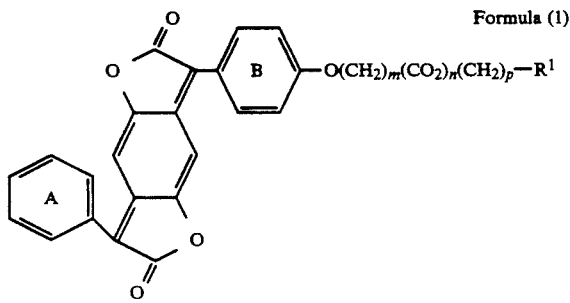

Formula (1)

wherein

Ring B is unsubstituted apart from the —O(CH$_2$)$_m$-(CO$_2$)$_n$)(CH$_2$)$_p$—$R^1$ or is substituted by from 1 to 4 further groups selected from the group consisting of —OH, —F, —Cl, —Br, nitro, $C_{1-4}$-aklyl, $C_{1-4}$-alkoxy, $C_{3-4}$-alkenyl, phenyl, naphthyl, $C_{1-4}$-alkoxy$C_{1-4}$-alkyl, $C_{1-4}$-alkoxya$C_{1-4}$-alkoxy, $C_{1-4}$-alkoxycarbonyl$C_{1-4}$-alkoxy, $C_{1-4}$-alkoxy carbonyl$C_{1-4}$-alkoxy, $C_{1-4}$-alkylcarbonyloxy$C_{1-4}$-alkoxy, phenoxy, napthoxy, $C_{1-4}$-alkylcarbonyl, $C_{1-4}$-alkylsulphonyl, CN—$C_{1-4}$-alkoxy, HO—$C_{1-4}$-alkoxy, HO$_2$C—$C_{1-4}$-alkoxy, $C_{1-4}$-alkylthio, phenylthio, naphthylthio and —NR$^2$R$^3$ in which R$^2$ and R$^3$ are each independently —H, $C_{1-4}$-alkyl or $C_{3-4}$-alkenyl, $R^1$ is cyclohexyl;

m is from 1 to 3;

n is 0;

p is 0; and

Ring A is unsubstituted or is substituted by $C_{1-4}$-alkoxy.

5. A polycyclic dye according to claims 1 to 2 wherein $R^1$ is cycloalkyl substituted by at least one group selected from $C_{1-6}$-alkyl, $C_{1-6}$-alkoxy, hydroxy, cyano, —Cl, —F, nitro, $C_{1-4}$-alkoxy-$C_{1-4}$-alkoxy, $C_{1-4}$-alkylcarbonyl, $C_{1-4}$-alkoxycarbonyl, $C_{1-4}$-alkoxy-$C_{1-4}$-alkoxycarbonyl, $C_{1-4}$-alkylcarbonyloxy, $C_{1-4}$-alkoxycarbonyloxy, $C_{1-4}$-alkoxy-$C_{1-4}$-alkoxycarbonyloxy, phenyl, amino, $C_{1-4}$-alkylamino and di($C_{1-4}$-alkyl)amino.

* * * * *